United States Patent [19]
Reif

[11] Patent Number: 5,716,402
[45] Date of Patent: Feb. 10, 1998

[54] HEART VALVE ROTATOR

[75] Inventor: Thomas H. Reif, Vero Beach, Fla.

[73] Assignee: Tri Technologies, Ltda (a BVI Corporation), Belo Horizonte, Brazil

[21] Appl. No.: 692,440

[22] Filed: Aug. 5, 1996

[51] Int. Cl.$^6$ ........................................ A61F 2/24
[52] U.S. Cl. ........................................ 623/2
[58] Field of Search ........................................ 623/2

[56] References Cited

U.S. PATENT DOCUMENTS

| | | | |
|---|---|---|---|
| 4,683,883 | 8/1987 | Martin | 623/2 |
| 5,236,450 | 8/1993 | Scott | 623/2 |
| 5,403,305 | 4/1995 | Sauter et al. | 623/2 |

FOREIGN PATENT DOCUMENTS

| | | | |
|---|---|---|---|
| 9515715 | 6/1995 | WIPO | A61B 8/12 |

*Primary Examiner*—John G. Weiss
*Assistant Examiner*—John M. Black
*Attorney, Agent, or Firm*—Albert H. Reuther

[57] ABSTRACT

A universal rotator for heart valve prothesis is provided including a heart valve rotator body having a handle portion that extends in a direction remote from a polycarbonate plastic rotator. The rotator body is suitably joined to the end of the handle and includes a transverse slot with semi-circular wedge-shaped extensions adapted to engage a mitral heart valve and an aortic heart valve for rotation. The rotator is used to spin a subassembly of a heart valve within a sewing cuff and locking ring to a more favorable position. The rotator can be used with both sides of the heart valve corresponding to either the mitral or aortic positions. The universal heart valve rotator for bileaflet mechanical heart prostheses can be used to rotate both mitral and aortic valves with a single instrument. The rotation instrument can be used to rotate a bileaflet mechanical heart valve prosthesis subassembly relative to a suture ring without substantial contact with the leaflets and to permit the leaflets to be fully examined between multiple use with the rotator.

10 Claims, 3 Drawing Sheets

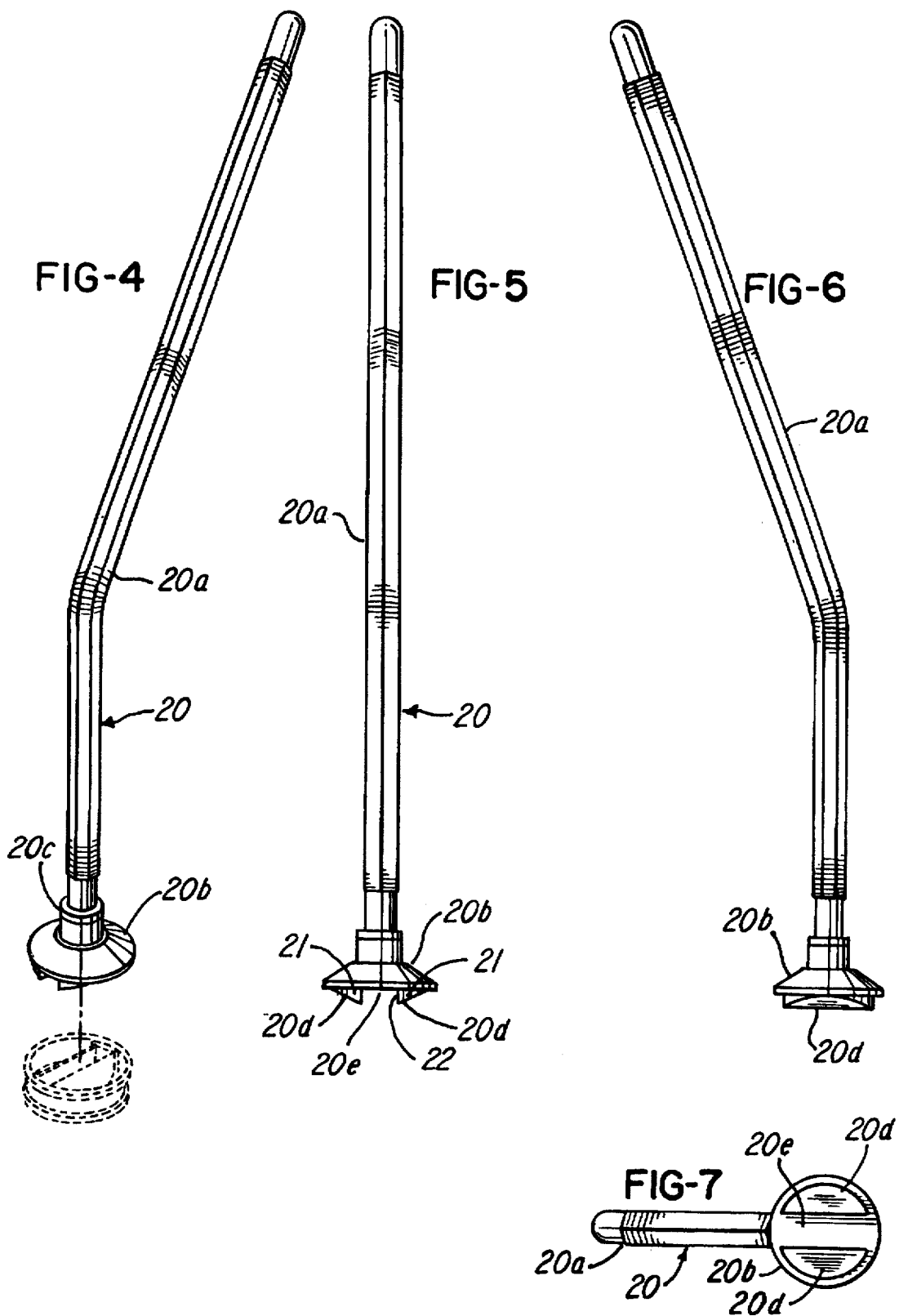

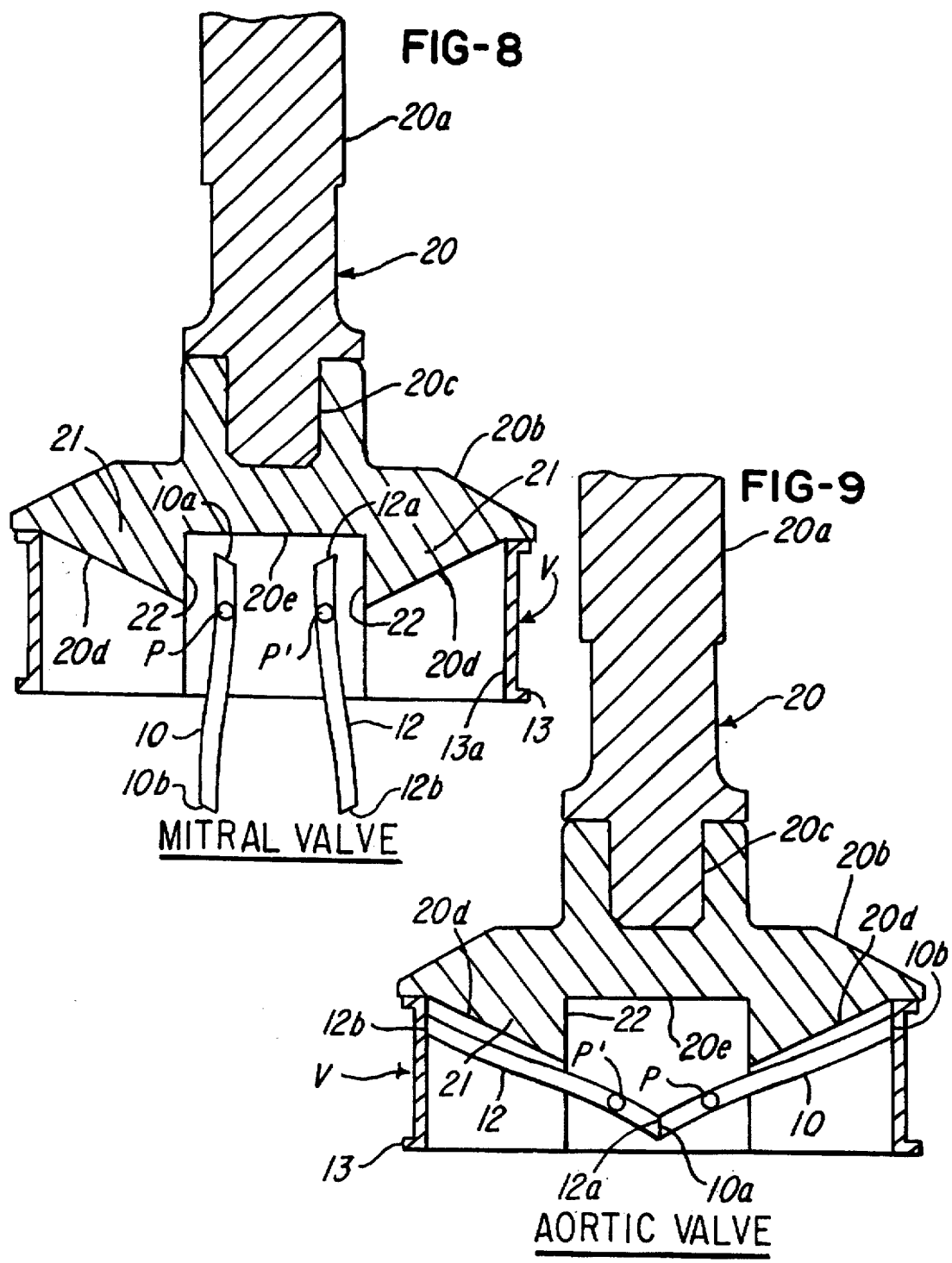

HEART VALVE ROTATOR

This application is based upon Design application Ser. No. 29/036,665 filed Mar. 24, 1995 for a Heart Valve Rotator, now U.S. Pat. No. Des. 372,781 issued on Aug. 13, 1996.

BACKGROUND OF THE INVENTION

1. Field of the Invention

The present invention relates to heart valve prostheses, and more particularly, to instruments for rotating the heart valve prostheses within their suture rings.

2. Description of the Prior Art

There are two types of heart valve prostheses, biological and mechanical. The medical indications for heart valve replacement are the same for both types. Examples include rheumatic heart disease, congenital anomalies, and myocardial infarction.

Unidirectional flow is the primary function of heart valve prostheses. This is usually accomplished by fashioning rigid or flexible leaflets, free to articulate within certain limitations, within an annular shaped frame, frequently referred to as an orifice ring. The restrained motion of these leaflets causes the flow to be essentially unidirectional, mimicking the natural function of native heart valves.

The present prior art disclosure dissertation will be limited to bileaflet mechanical valves, such as disclosed in U.S. Pat. No. 4,689,046-Bokros dated Aug. 25, 1987 and U.S. Pat. No. 4,950,287-Reif dated Nov. 12, 1991. The leaflets of mechanical valves are usually constructed of pyrolytic carbon or a composite of pyrolytic carbon and a substrate, such as graphite or titanium. The leaflets are typically constrained within an orifice ring also constructed of the same materials. The orifice ring with the inserted leaflets is often referred to as a subassembly. The subassembly is usually attached to the heart by using a biocompatible fabric material, such as DACRON™. The fabric material is usually purchased or fashioned into a tubular configuration. It is then folded into an annular configuration often referred to as the suture ring. Sometimes annular shaped filler rings, often constructed of TEFLON™ or SILASTIC™, are inserted within the folded portion of the fabric tube in order to make the suture ring larger and/or more compliant. DACRON™ is a trademark used for a synthetic polyester material also referred to as an American equivalent of terylene synthetic fiber material; TEFLON™ is a trade name for polytetrafluoroethene designated by this trademark used for a waxy opaque material; and SILASTIC™ is a trade name for a range of silicon rubbers noted for very good heat resistance and a wide temperature range of application with excellent chemical resistance and electrical properties. It is desirable that a suture ring be rotatable relative to the subassembly, as this feature greatly facilitates implantation into the heart and enhances the safety of the device.

Significant forces are applied to the subassembly, when it is rotated relative to the suture ring, during the surgical implantation of the heart valve. It is, therefore, important that the instruments used to rotate the subassembly be carefully designed, in order to prevent damage to the subassembly. One public domain solution has been used by several manufacturers. Two different types of instruments, often called rotators, are designed to fit into the inside diameter of the orifice ring. One type fits into the inflow side of the orifice ring (for the rotation of mitral heart valve prostheses) and the other fits into the outflow side of the orifice ring (for the rotation of aortic heart valve prostheses). Both the inflow and outflow rotators are shaped so that they avoid contact with the leaflets, as the pivot mechanism can be easily damaged during rotation. A disadvantage to this method is that two different rotators are required, depending upon whether a mitral or an aortic valve is being replaced.

U.S. Pat. No. 5,443,502-Caudillo et al dated Aug. 22, 1995 discloses a rotatable heart valve holder representing a slight modification of another public domain solution. Heart valve prostheses are usually mounted on injection molded plastic parts, called holders, when they are packaged. Typically, the public domain holders have two opposed substantially mirror-image halves which are joined by a hinge. Two jaws outwardly engage the inside circumferential surface of the orifice ring. A suture is usually tied around the hinge area to prevent the jaws from disengaging the orifice ring. The U.S. Pat. No. 5,443,502 holder is very similar to this public domain solution, the major difference being that the holder is sutured to the suture ring, making it both a holder and a rotator. It might be of interest to note that many public domain solutions for biological heart valve holders suture the holders to the suture ring. This is because the flexible leaflets are attached to the inside circumferential surface of the orifice ring and outwardly expanding jaws cannot be used without damaging the leaflets. The major disadvantage to the disclosure of U.S. Pat. No. 5,443,502 is that most surgeons prefer to visualize the leaflets prior to the rotation of the subassembly and this is not possible with the design.

U.S. Pat. No. 5,480,425-Ogilive dated Jan. 2, 1996 discloses another combination holder-rotator. It too suffers from the same limitations as the disclosure of U.S. Pat. No. 5,443,502 with regard to the visualization of the leaflets prior to rotation. Additionally, the disclosure of U.S. Pat. No. 5,480,425 is relatively complicated and expensive to manufacture.

In summary, there are several disadvantages to the current prior art design configurations of rotators in heart valve prostheses. Some designs are inadequate because they require separate instruments for mitral and aortic valve surgeries. Other designs fail to permit the full visualization of the leaflets within the orifice ring prior to the rotation of the subassembly. Further, some designs are complicated and expensive to manufacture.

SUMMARY OF THE INVENTION

A universal rotator for bileaflet mechanical heart valve prostheses is disclosed which can be used to rotate both mitral and aortic valves with a single instrument. The rotator fits into either the inflow or the outflow side of the orifice ring. The rotator is designed such that it does not contact the leaflets for either the mitral or the aortic applications, thus, protecting the delicate pivot mechanism from damage during rotation. The rotator can be used, removed for full visualization of the leaflets, and reapplied as deemed necessary by the implanting surgeon. Also, the rotator has a simple configuration, making it easy and inexpensive to manufacture.

With the foregoing in mind, it is an object of the present invention to provide a single universal rotator for a bileaflet mechanical heart valve prosthesis which can be used for either mitral or aortic applications.

It is also an object of the present invention to provide a single universal rotator for a bileaflet mechanical heart valve prosthesis which can be used to rotate the subassembly relative to the suture ring without substantial contact with the leaflets.

Another object of the present invention is to provide a single universal rotator for a bileaflet mechanical heart valve prosthesis which permits the leaflets to be fully examined between multiple uses with the rotator.

A further objective of the present invention is to provide a single universal rotator for a bileaflet mechanical heart valve prosthesis which is easy and inexpensive to manufacture.

Other objects and advantages of the present invention, will become apparent from the following detailed description, taken with reference to the accompanying drawings.

BRIEF DESCRIPTION OF THE DRAWINGS

FIG. 4 shows a perspective view of the universal heart valve rotator.

FIG. 5 shows a front elevational view of the universal heart valve rotator.

FIG. 6 shows a side elevational view of the universal heart valve rotator.

FIG. 7 shows a bottom plan view of the universal heart valve rotator.

FIG. 8 shows a cross-sectional view of the universal rotator inserted into the inflow side of a bileaflet mechanical heart valve prosthesis subassembly.

FIG. 9 shows a cross-sectional view of the universal rotator inserted into the outflow side of a bileaflet mechanical heart valve prosthesis subassembly.

DESCRIPTION OF THE PREFERRED EMBODIMENTS

Figure 1:
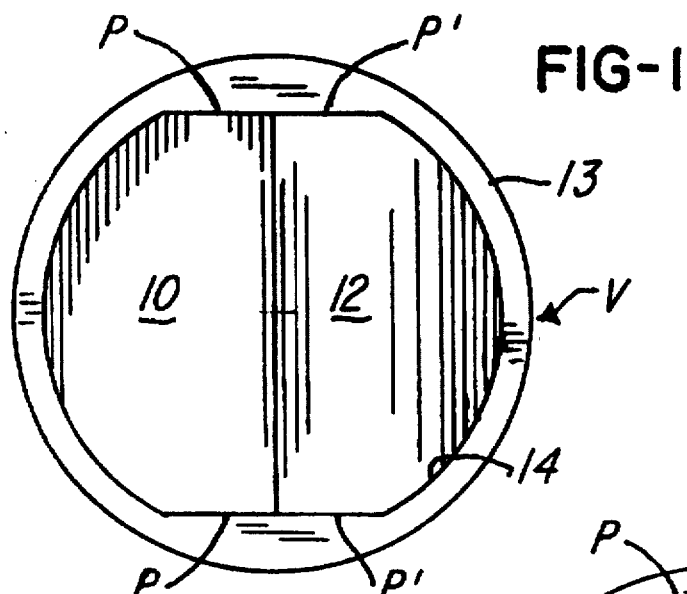
FIG. 1 shows a top or inflow view of a bileaflet mechanical heart valve prosthesis subassembly with the leaflets in the fully closed position.

The following description is of the best mode presently contemplated for practicing the invention. This description is not to be taken in a limiting sense, but is made for the purpose of describing the general principles of the invention. The scope of the invention should be determined with reference to the claims. The preferred embodiment of the present invention will now be described with reference to the accompanying drawings. In the drawings, like numerals will be used to designate like parts throughout.

FIG. 1 depicts a plan view of a bileaflet mechanical heart valve prosthesis subassembly V as seen from an inflow or top direction. The suture ring is omitted in this figure to simplify the present discussion. A pair of leaflets 10 and 12 are housed within an annular shaped orifice ring 13. The leaflets 10 and 12 are constrained within the orifice ring 13 such that they are free to rotate about pivots P and P'. In this view, the leaflets 10 and 12 are shown in the fully closed position, blocking the orifice 14 in the orifice ring 13.

Figure 2:
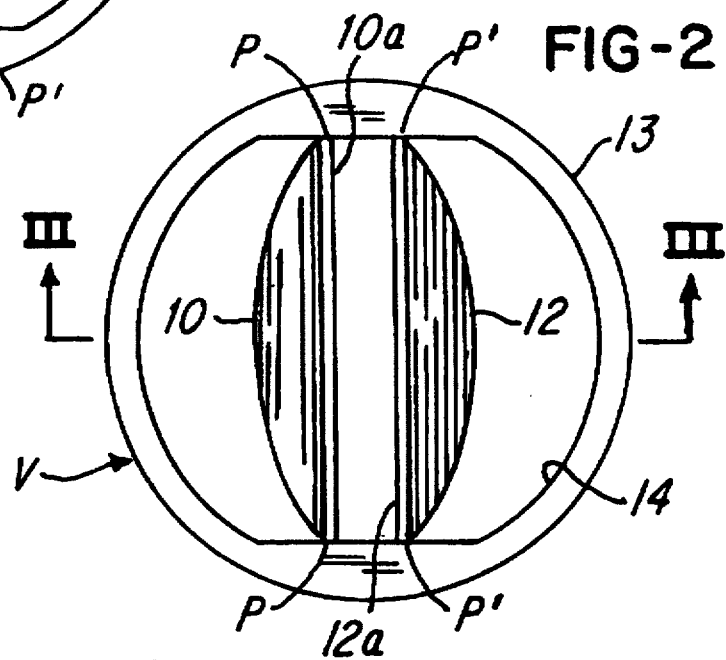
FIG. 2 shows a top or inflow view of a bileaflet mechanical heart valve prosthesis subassembly with the leaflets in the fully open position.

In FIG. 2, the leaflets 10 and 12 are again shown from an inflow or top direction. However, the leaflets 10 and 12 are shown in the fully open position. The leaflets 10 and 12 have leading edges 10a and 12a that are beveled to permit a reasonably tight seal at the contact surface between the leaflets 10 and 12.

The orifice ring has an annularly shaped inner wall surface 13a and substantially parallel, non-annularly shaped inner wall surfaces 13b as seen in FIG. 2. The inner wall surfaces 13b are located at the regions of the orifice ring containing the pivots P and P'.

Figure 3:
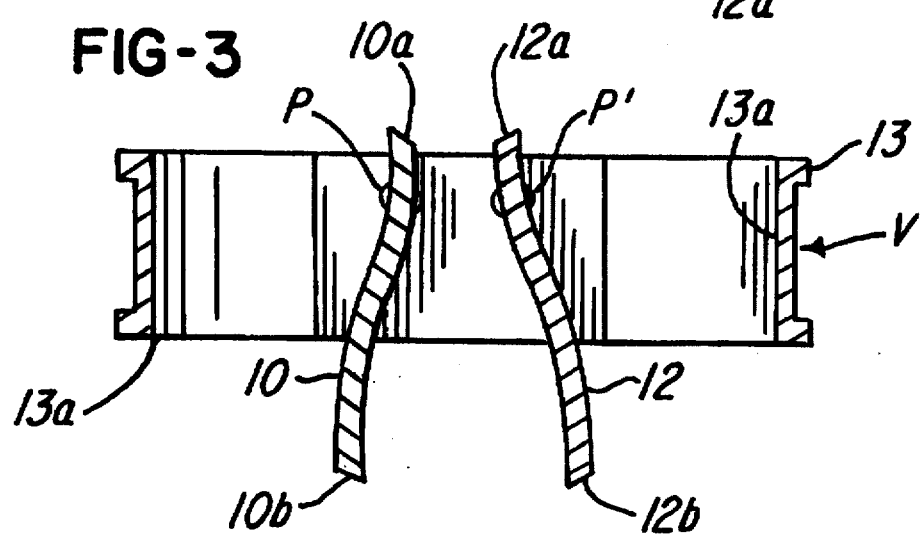
FIG. 3 shows a cross-sectional view of a bileaflet mechanical heart valve prosthesis subassembly taken along line III—III as shown in FIG. 2.

The subassembly V is shown in cross-section in FIG. 3, with the leaflets 10 and 12 fully open. The leaflets 10 and 12 have trailing edges 10b and 12b that are also beveled to permit a reasonably tight seal with the inner wall surface 13a of the orifice 14 in the orifice ring 13.

The universal rotator 20 is shown in perspective view in FIG. 4. The rotator 20 has a handle 20a and a generally cylindrical shaped head 20b. The handle 20a is shown here as being separable from the head 20b by using threads 20c at the junction of the handle 20a and the head 20b. Other methods of attachment are possible and the handle 20a may even be integral with the head 20b.

The head 20b has two generally triangular shaped protrusions 21, each protrusion having end surfaces 20d and engaging surfaces 22, as depicted in the front elevational view FIG. 5. The head 20b also has a generally rectangular shaped groove 20e. For further clarity, FIGS. 6 and 7 depict these same features in side elevational and bottom plan views, respectively.

Mode of Operation

The universal rotator 20 is shown cross-section in FIG. 8 after insertion into the inflow side of a subassembly V. The rectangular groove 20e is designed to always give clearance to the leaflets 10 and 12, including their leading edges 10a and 10b. The end surfaces 20d are designed to have a clearance fit with the orifice 14 of the orifice ring 13. Rotation of the head 20b relative to the subassembly V, causes contact of the engaging surfaces 22 of the triangular protrusions 21 with the inner wall surface 13b of the orifice 14 in the orifice ring 13. No contact occurs between the head 20b and the leaflets 10 and 12. This avoids damaging the pivot mechanism P and P'.

The universal rotator 20 is again shown in cross-section in FIG. 9, this time after insertion into the outflow side of a subassembly V. The end surfaces 20d are designed to always give clearance to leaflets 10 and 12, including their trailing edges 10b and 12b. Again, the end surfaces 20d are designed to have a clearance fit with the orifice 14 of the orifice ring 13. Rotation of the head 20b relative to the subassembly V, causes contact of the engaging surfaces 22 of the triangular protrusions 21 with the inner wall surface 13b of the orifice 14 in the orifice ring 13. No contact occurs between the head 20b and the leaflets 10 and 12. This avoids damaging the pivot mechanism P and P'.

The universal rotator 20 provides a single instrument for use with bileaflet mechanical heart valve prostheses, which can be used for either mitral (FIG. 8) or aortic applications (FIG. 9). It is possible to rotate the subassembly V relative to the suture ring without substantial contact with the leaflets 10 and 12. This method permits the leaflets 10 and 12 to be fully examined between multiple uses with the rotator 20. Also, the instrument is easy and inexpensive to manufacture.

In conclusion, the heart valve rotator of the present invention serves as a universal rotator for heart valve prostheses including many possibilities for a handle portion that is short and straight; that is long and curved; that is plastic at one end joined by a deformable wire to a plastic rotator end, as well as one that is offset at an angle in a direction remote from a polycarbonate plastic rotator per se integral or suitably joined such as by a thread to the end of the handle and including a transverse slot with semi-circular wedged-shaped extensions of the rotator per se adapted to engage a mitral heart valve for rotation as well as an aortic heart valve for rotation. The rotator is used to spin a subassembly of a heart valve within a sewing cuff and locking ring as a surgeon sometimes does after sewing a final assembly into a heart of a patient. This heart valve rotator having the tool handle therewith allows rotation of the subassembly to a more favorable position. The rotator can be used from both sides of the heart valve including either top or bottom corresponding to either the aortic or mitral positions of the heart valve. The heart valve rotator can be used for example with features of co-pending applications including a heart valve as disclosed by Design Ser. No. 036,687-Reif filed Mar. 24, 1995 as well as a heart valve locking ring of Design Ser. No. 036,662-Reif filed Mar. 24, 1995, and also with earlier disclosure of a heart valve pivot arrangement of U.S. Design Pat. No. D-358,648-Reif dated May 23, 1995. The heart valve rotator has a configuration set forth in detail by the foregoing specification.

The present invention is, of course, in no way restricted to the specific disclosure of the specification and drawings, but also encompasses any modifications within the scope of the appended claims.

What I claim is:

1. A universal heart valve rotator comprising a body including a handle portion that extends in a direction remote from a plastic rotator portion, fastening means configured to join an end of said handle portion in complementary relationship with said rotator portion, said rotator portion having semi-circular wedge-shaped extensions for engaging against substantially parallel, non-annular inner wall surfaces of either an inflow or outflow side of an orifice ring of a bileaflet heart valve for rotating movement of the heart valve without any contact between the head and the heart valve leaflets.

2. The universal heart valve rotator according to claim 1, in which said semi-circular wedge-shaped extensions are sized and configured to be used directly against an orifice ring of a bileaflet heart valve to rotate said orifice relative to a suture ring without any substantial contact against the heart valve leaflets.

3. The universal heart valve rotator according to claim 1, in which said fastening means between handle portion and rotator portion are directly complementary joinder portions.

4. The universal heart valve rotator according to claim 3, in which the rotator portion being threadably connected to said handle portion has a generally cylindrical shaped head and said rotator portion directly by threaded portions complementary to each other.

5. The universal heart valve rotator according to claim 1, in which said handle portion and said rotator portion are integral.

6. The universal heart valve rotator according to claim 4, in which said plastic rotator portion has a generally rectangular shaped diametrical groove formed therein said groove extends transversely and having a depth for mitral leaflet clearance.

7. The universal heart valve rotator according to claim 6, in which said rectangular shaped groove and a recessed outer periphery of said rotator portion having a depth to allow for a clearance fit for an orifice ring.

8. The universal heart valve rotator according to claim 7, in which said semi-circular wedge-shaped extensions have end surfaces, said end surfaces provide a clearance fit for an orifice of an orifice ring of a bileaflet heart valve.

9. The universal heart valve rotator according to claim 5, in which said handle portion and said rotator portion are of solid plastic material.

10. The universal heart valve rotator according to claim 9, in which said handle portion is flexably deformable.

* * * * *